United States Patent
Rennie

[11] 4,018,221
[45] Apr. 19, 1977

[54] SUPPORT FOR ANESTHETIC GAS DELIVERY HOSES AND ENDOTRACHEAL TUBES

[76] Inventor: Thomas Rennie, 335 Dewey St., Bennington, Vt. 05201

[22] Filed: Sept. 29, 1975

[21] Appl. No.: 617,716

[52] U.S. Cl. .............................. 128/185; 128/188; 128/DIG. 26; 128/206; 128/140 R
[51] Int. Cl.² ...................................... A61M 25/02
[58] Field of Search ............ 128/DIG. 26, DIG. 15, 128/188, 185, 133, 134, 157, 158, 160, 163, 165, 169, 289, 290 R, 290 H, 296, 327, 348 R, 349 R, 351, 140 R, 145.5–145.8; 269/3, 322; 2/DIG. 11

[56] References Cited
UNITED STATES PATENTS

| | | | |
|---|---|---|---|
| 3,256,882 | 6/1966 | Huber | 128/169 |
| 3,586,001 | 6/1971 | Sanderson | 128/DIG. 15 |
| 3,765,421 | 10/1973 | Poprik | 128/DIG. 26 |
| 3,880,161 | 4/1975 | Fossel | 128/DIG. 15 |
| 3,942,525 | 3/1976 | Dragan | 128/165 |

Primary Examiner—Robert W. Michell
Assistant Examiner—Henry J. Recla
Attorney, Agent, or Firm—Clarence A. O'Brien; Harvey B. Jacobson

[57] ABSTRACT

An elongated flexible strap of predetermined width is provided and includes opposite end portions. The strap may be encircled about a portion of a patient's body and one end of the strap includes a first fastening structure on one side thereof facing outwardly from the strap while the other end portion of the strap includes a second fastening structure on the other side thereof also facing outwardly of the strap. The first and second fastening structures are releasably engageable with each other in adjusted end overlapped positions of the opposite end portions of the strap and the second fastening structure is spaced from the corresponding terminal end of the strap with a thick, bendable and somewhat deformable but shape retentive pad being secured over and extending along the other side of the strap between the second fastening structure and the corresponding terminal end of the strap. The opposing surfaces of the pad and the portion of the strap spaced therealong toward the other end of the strap from the first fastening structure and overlapping the outer side of the pad define friction surfaces between which anesthetic gas delivery hoses may be clamped.

2 Claims, 4 Drawing Figures

SUPPORT FOR ANESTHETIC GAS DELIVERY HOSES AND ENDOTRACHEAL TUBES

BACKGROUND OF THE INVENTION

Various forms of paraphernalia have been heretofore provided for supporting endotracheal tubes and anesthesia delivery hoses from the head of a patient. Examples of various forms of support structures designed for this purpose are disclosed in U.S. Pat. Nos. 3,464,411, 3,602,227, 3,713,484, 3,774,616 and 3,827,433.

However, previous support devices for endotracheal tubes and anesthesia hoses sometimes involve the utilization of tape which tends to become loosened as well as other attaching devices which may require adjustment or applied pressure by at least one hand of the anesthesiologist. In addition, support structures for endotracheal tubes and anesthesia hoses as utilized in the past often result in the oral endotracheal tube, anesthesia hoses and/or nasoendotracheal tube being sufficiently loosely supported to allow severe pressure to be exerted on the tissues of the patient contacted by the tubes or hoses. Most importantly, previously patented devices for supporting endotracheal tubes and anesthetic gas delivery hoses all obscure the face, oral area and/or jaws thereby preventing their use during anesthesia for surgery on these regions. The instant device works equally well with oral as well as nasal endotracheal tubes.

BRIEF DESCRIPTION OF THE INVENTION

The support of the instant invention comprises an enlongated flexible strap of predetermined length and width with opposite sides of the opposite ends of the strap provided with strips of "Velcro" secured thereto. One of the Velcro strips is spaced from the corresponding terminal end of the strap and that terminal end has a thick somewhat flexible and deformable pad secured thereto on the same side as the adjacent Velcro strip. The strap may be encircled about a portion of a patient's body, such as the patient's head, and the opposite end portions of the strap may be overlapped with the Velcro strips engaged with each other securing the strap about the patient's head. The overlapped portions of the pad and opposite end portion of the strap define opposing friction surfaces between which anesthesia hoses, etc., may be clamped for stationary support from the patent's head.

The main object of this invention is to provide a support for endotracheal tubes, anesthesia hoses and nasoendotracheal tubes, etc.

Another object of this invention is to provide a patient mounted support for various tubes and/or hoses which may be readily adjusted to the size of the portion of the patient's body about which the strap portion of the support to be secured.

Yet another object of this invention is to provide an adjustable length strap structure which may also be utilized to support various other paraphernalia, such as nasoesophageal temperature probes and which may further be used as a temporary support, prior to reduction and fixation, for mandibular and/or mid-face fractures in lieu of the more conventionally utilized Barton bandage.

Another very important object of this invention is to provide an apparatus which may be utilized as a pressure dressing subsequent to surgery on the lateral face and jaws.

A final object of this invention to be specifically enumerated herein is to provide an apparatus in accordance with the preceding objects and which will conform to conventional forms of manufacture, be of simple construction and easy to use, so as to provide a device that will be economically feasible, long lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

DETAILED DESCRIPTION OF THE INVENTION

Figure 1:
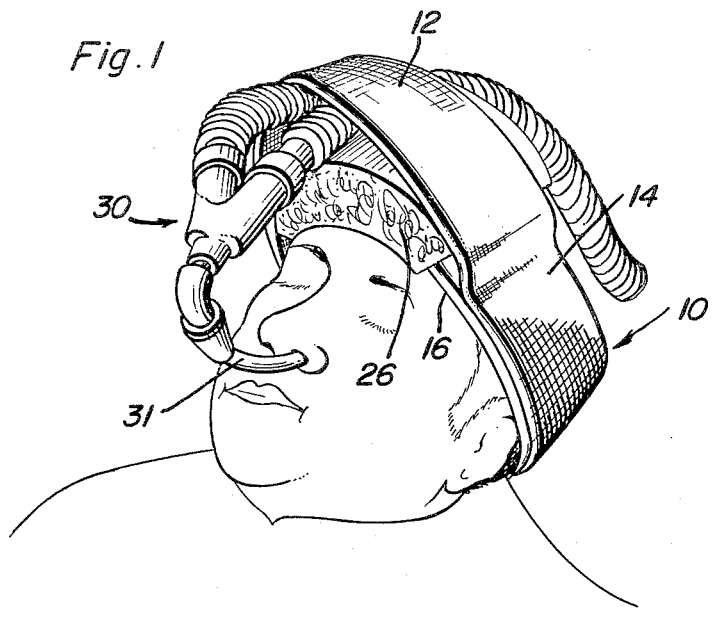
FIG. 1 is a perspective view of the instant invention in use supporting an anesthetic gas delivery assembly from the head of a patient.

Referring now more specifically to the drawings, the numeral 10 generally designates the support of the instant invention. The support 10 includes an elongated flexible strap 12 of predetermined width and length. The strap 12 includes first and second end portions 14 and 16. The first end portion 14 has an elongated strip 18 of Velcro secured to one side 20 of the strap 12 and the other end portion 16 of the strap 12 has a second strip 22 of Velcro secured to the other side 24 of the strap 12 at a point spaced from the adjacent terminal end of the strap.

An arcuate thick pad 26 constructed of shape retentive but deformable and resilient material is secured to the terminal end of the end portion 16 of the strap 12 on the side 24 thereof closely adjacent the second Velcro strip 22. If it is desired, the pad 26 may be secured to the strap 12 in a manner enabling ready removal of the pad 26.

Figure 2:
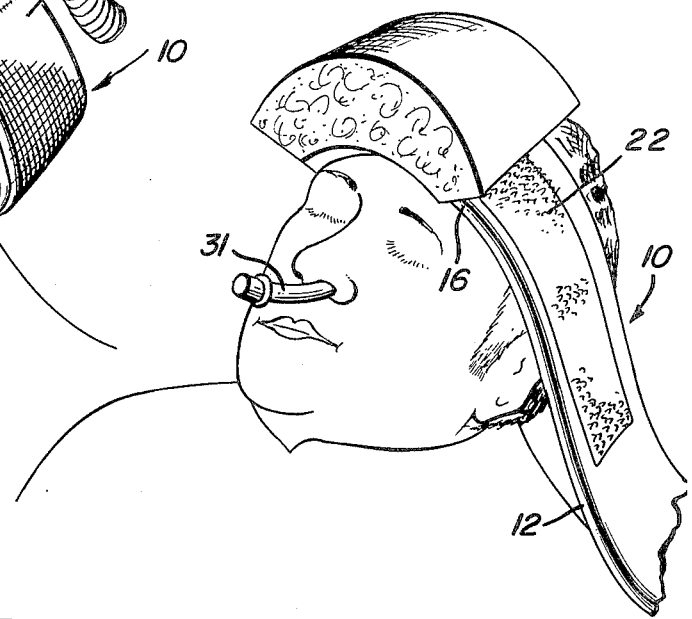
FIG. 2 is a view similar to FIG. 1 but illustrating the apparatus as initially applied to the head of a patient.
Figure 3:
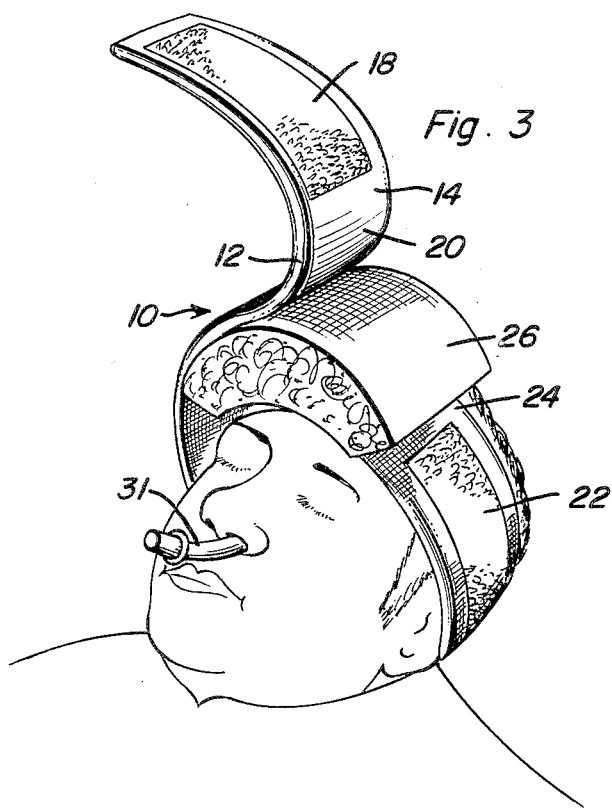
FIG. 3 is a further perspective view similar to FIG. 1 but with the apparatus in a position of application to the patient's head intermediate the positions thereof illustrated in FIGS. 1 and 2.
Figure 4:
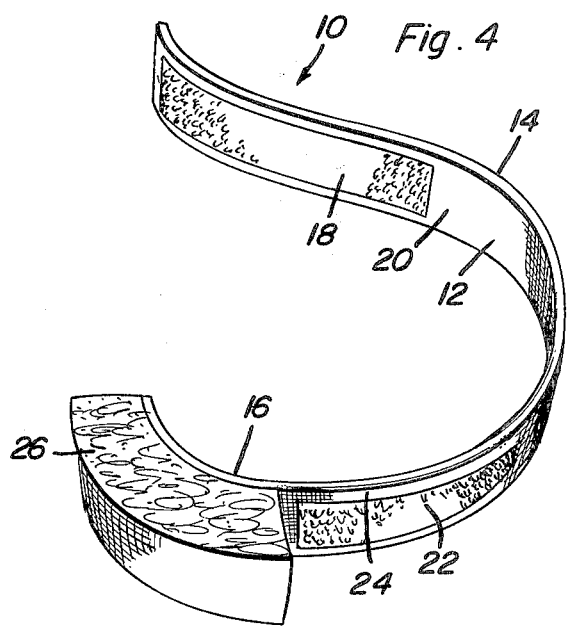
FIG. 4 is a perspective view of the apparatus in a non-applied position.

In operation, the side 20 of the end portion 16 of the strap 12 is placed over the forehead of a patient as illustrated in FIG. 2 of the drawings with the pad 26 carried by the end portion 16 disposed on the upper side 24 of the strap 12. Then, the strap 12 is passed downardly along the left side of the patient's head, in back of his head and then up along the right side of the patient's head with the end portion 14 overlying the pad 26 in the manner illustrated in FIG. 3. Thereafter, the terminal end of the strap 12 to which the strip 18 is secured is placed downwardly over the outwardly facing strip 22 of Velcro whereby the Velcro strips 18 and 22 will removably attach themselves to each other with the strap 12 encircling the patent's head substantially one and 1/2 times.

Prior to the end portion 14 of the strap 12 being secured over the strip 22 of Velcro, an anesthetic gas delivery structure referred to in general by reference numeral 30 or any other tube or hose structure may be placed over the upper outer surface of the pad 26 so that when then end portion 14 is fastened in position in the manner illustrated in FIG. 1 of the drawings, the structure 30 will be clamped between the pad 26 and the end portion 14 of the strap 12. In this manner, the structure 30 will be securely fastened in position and the associated endotracheal tube 31 passing into the head cavity may be properly positioned so as not to exert severe pressure upon the body tissues contacted thereby.

If it is desired, the strap 12 may be used as a pressure bandage as herinbefore set forth and may also be used on other parts of the body. Further, the strap 12 may also be used to support such paraphernalia as nasogastric and nasoesophageal temperature probes, etc. Still further, the strap 12 may be used as a temporary support, prior to reduction and fixation, for maxillary and/or mandibular fractures. Finally, the strap 12 may be used as a pressure dressing subsequent to surgery on the lateral face or jaws and a greatly expanded version could be used as an abdominal binder subsequent to abdominal surgery, in each of the above noted usages of the strap 12, the pad 26 may be removed.

The pad 26 is preferably constructed of polyurethane, although other suitable materials may also be used and the strap 12 may be constructed of polyurethane, although other suitable materials may also be used in this instance.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A medical band for supporting endotracheal tubes and anesthesia hoses from the forward head portion of a patient, said band comprising an elongated flexible strap of predetermined width, said strap including opposite end portions and being of a length to encircle substantially one and one-half times about a patient's head, one terminal end portion of said strap including a first Velcro strip on one side facing outwardly therefrom, the other end portion of said strap including a second Velcro strip on the other side thereof facing outwardly thereof and spaced from the corresponding terminal end portion, said first and second strips being releasably engageable with each of adjusted end overlapped positions of said one terminal end portion and said other end portion, a thick, arcuate and somewhat deformable but shape retentive pad secured over and extending along said other side of said strap between said second fastening means and said terminal end of said other end of said strap and over which the zone of said one end portion of said strap spaced along the latter from said one terminal end portion may be lapped, said zone of said one end portion and the opposition surfaces of said pad define opposing friction surfaces between which anesthetic gas delivery hoses may be clamped.

2. The combination of claim 1 wherein said Velcro strips are of less width than said strap and spaced at least slightly from the opposite longitudinal edges of said strap.

* * * * *